(12) United States Patent
Dietzel et al.

(10) Patent No.: US 8,435,497 B2
(45) Date of Patent: May 7, 2013

(54) FORMOTEROL OF AND CICLESONIDE COMBINATION

(75) Inventors: Klaus Dietzel, Constance (DE); Helgert Mueller, Radolfzell (DE)

(73) Assignee: Takeda GmbH, Constance (DE)

( * ) Notice: Subject to any disclaimer, the term of this patent is extended or adjusted under 35 U.S.C. 154(b) by 1660 days.

(21) Appl. No.: 10/559,383

(22) PCT Filed: Jun. 9, 2004

(86) PCT No.: PCT/EP2004/051067
§ 371 (c)(1), (2), (4) Date: Dec. 6, 2005

(87) PCT Pub. No.: WO2004/110460
PCT Pub. Date: Dec. 23, 2004

(65) Prior Publication Data
US 2006/0127323 A1    Jun. 15, 2006

(30) Foreign Application Priority Data

Jun. 13, 2003 (EP) .................................. 03013510

(51) Int. Cl.
| | |
|---|---|
| *A61K 9/12* | (2006.01) |
| *A61K 9/14* | (2006.01) |
| *A61K 31/00* | (2006.01) |
| *A61K 31/12* | (2006.01) |
| *A61K 31/13* | (2006.01) |
| *A61K 31/075* | (2006.01) |
| *A61K 31/205* | (2006.01) |
| *A61K 31/21* | (2006.01) |
| *A61K 31/33* | (2006.01) |
| *A61K 31/58* | (2006.01) |

(52) U.S. Cl.
USPC .............. 424/45; 424/46; 514/174; 514/183; 514/510; 514/555; 514/649; 514/653; 514/675; 514/678; 514/681; 514/715; 514/717; 514/729

(58) Field of Classification Search .................... 424/45, 424/46; 514/174, 183, 510, 555, 649, 63, 514/675, 678, 681, 715, 717, 729
See application file for complete search history.

(56) References Cited

U.S. PATENT DOCUMENTS

| | | | |
|---|---|---|---|
| 3,994,974 A | 11/1976 | Murakami et al. | |
| 5,434,304 A * | 7/1995 | Trofast et al. | 564/221 |
| 5,474,759 A * | 12/1995 | Fassberg et al. | 424/45 |
| 5,482,934 A | 1/1996 | Calatayud et al. | |
| 5,733,901 A | 3/1998 | Gutterer | |
| 5,795,564 A | 8/1998 | Aberg et al. | |
| 6,068,833 A | 5/2000 | Aberg et al. | |
| 6,413,497 B1 | 7/2002 | Weil et al. | |
| 6,475,467 B1 | 11/2002 | Keller et al. | |
| 2002/0030068 A1 * | 3/2002 | Burt | 222/402.1 |
| 2005/0245493 A1 | 11/2005 | Marx et al. | |

FOREIGN PATENT DOCUMENTS

| | | |
|---|---|---|
| DE | 41 29 535 A1 | 3/1992 |
| DE | 195 41 689 A1 | 5/1996 |
| DE | 19541689 A1 | 5/1996 |
| EP | 0 372 777 B1 | 6/1990 |
| EP | 0 504 112 A2 | 9/1992 |
| EP | 0 553 298 B1 | 8/1993 |
| GB | 247680 | 2/1926 |
| WO | 91/04011 A1 | 4/1991 |
| WO | 91/11173 A1 | 8/1991 |
| WO | 91/11495 A1 | 8/1991 |
| WO | 91/14422 A1 | 10/1991 |
| WO | 92/11190 A2 | 7/1992 |
| WO | 93/11743 A1 | 6/1993 |
| WO | 93/11745 A1 | 6/1993 |
| WO | 93/11747 A1 | 6/1993 |
| WO | 94/22899 A1 | 10/1994 |
| WO | 96/32150 A1 | 10/1996 |
| WO | 97/47286 A1 | 12/1997 |
| WO | 98/21175 A1 | 5/1998 |
| WO | 98/52542 A1 | 11/1998 |
| WO | 99/17754 A1 | 4/1999 |
| WO | 00/07567 A1 | 2/2000 |
| WO | WO 01/78738 * | 10/2001 |
| WO | 02/30394 A2 | 4/2002 |
| WO | 2004/052374 | 6/2004 |
| WO | 2004/103379 A1 | 12/2004 |
| WO | 2004/105727 A2 | 12/2004 |
| WO | 2005/004853 A1 | 1/2005 |
| WO | 2005/034911 A1 | 4/2005 |

OTHER PUBLICATIONS

Vippagunta et al. "Crystalline Solids," Advanced Drug Delivery Reviews, 2001, 48, 1-26.*
Braga et al. Chem. Commun., "Making Crystals from Crystals: a green route to crystal engineering and polymorphism," 2005, pp. 3635-3645.*
Garcia-Marcos et al. "Inhaled corticosteroids plus long-acting beta2-agonists as combined therapy in asthma," Expert Opin. Pharmacother., Apr. 2003, 4(1), pp. 23-39.*

* cited by examiner

*Primary Examiner* — James H Alstrum Acevedo
(74) *Attorney, Agent, or Firm* — Nath, Goldberg & Meyer; Joshua B. Goldberg; Sheldon M. McGee

(57) ABSTRACT

The invention relates to pharmaceutical compositions containing combinations of formoterol and ciclesonide and the use of such pharmaceutical compositions in medicine, in particular, the prophylaxis and treatment of respiratory disease.

1 Claim, No Drawings

FORMOTEROL OF AND CICLESONIDE COMBINATION

FIELD OF THE INVENTION

This invention relates to pharmaceutical compositions containing combinations of formoterol and ciclesonide and the use of such pharmaceutical compositions in medicine, in particular in the prophylaxis and treatment of respiratory disease.

BACKGROUND

Formoterol which is the compound N-[2-hydroxy-5-(1-hydroxy-2-((2-(4-methoxyphenyl)-1-methylethyl)amino)ethyl)phenyl] formamide, is known from U.S. Pat. No. 3,994,974. It is known to be a bronchodilator and used in the treatment of inflammatory or obstructive airways diseases.

GB 247680 discloses pregna-1,4-diene-3,20-dione-16-17-acetal-21 esters and their use in the treatment of inflammatory conditions. The compounds have the general structure:

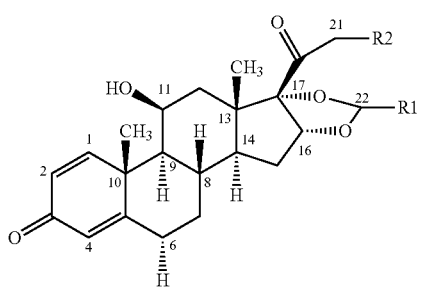

Formula I wherein R1 is 2-propyl, 1-butyl, 2-butyl, cyclohexyl or phenyl; and R2 is acetyl or isobutanoyl. Ciclesonide is the INN for a compound of formula I in which R1 is cyclohexyl and R2 is isobutanoyl with the chemical name [11β,16α(R)]-16,17-[(Cyclohexylmethylen)bis(oxy)]-11-hydroxy-21-(2-methyl-1-oxopropoxy)pregna-1,4-dien-3,20-dion.

This compound has undergone evaluation as an antiasthmatic and pharmacokinetic studies show that it will be useful in an inhaler formulation. Ciclesonide is only moderately absorbed after oral administration and has low systemic activity. Concentration of the drug in the lungs is high and metabolism by liver oxidases is very high, giving the drug a low plasma half-life. Systemic activity of ciclesonide is three times lower than that of budesonide, but anti-inflammatory activity is higher for the former.

DE 19541689 is related to the combined use of ciclesonide with a β-sympathomimetic, for the treatment of disorders of the respiratory tract. As an example a metered dose aerosol composition comprising ciclesonide and formoterol in tricholorofluoromethane (R11) as propellant is disclosed.

EP-A-0504112 discloses examples of pharmaceutical compositions for aerosol use comprising formoterol fumarate.

WO 93/11747 discloses a pharmaceutical suspension formulation suitable for aerosol administration, consisting essentially of a therapeutically effective amount of a drug and a propellant selected from the group consisting of HFA 134a, HFA 227, and a mixture thereof, the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug. The application specifically discloses formulations of formoterol fumarate in HFA 134a, HFA 227 and 1:1 mixtures of HFA 134a and HFA 227.

WO 93/11745 discloses pharmaceutical aerosol formulations, substantially free of surfactant containing fluorocarbon or hydrogen-containing chlorofluorocarbon propellants and up to 5% of a polar co-solvent. Preferred propellants are HFA 134a and HFA 227, which are preferably used alone. The preferred polar co-solvent is ethanol and it is stated that in general only small quantities e.g. 0.05 to 3.0% w/w of polar co-solvent are required to improve the dispersion and the use of quantities in excess of 5% w/w may dis-advantageously tend to dissolve the medicament.

WO 97/47286 discloses a pharmaceutical suspension formulation suitable for aerosol administration, consisting essentially of: (a) from 0.0025 to 0.1% w/v of micronized formoterol, or an acid addition salt thereof and (b) from 0.1 to 5.0% w/v ethanol, (c) HFA 134a, HFA 227 or a mixture of HFA 227 and HFA 134a and optionally (d) a surfactant other than a monoacetylated or diacetylated monoglyceride, the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug. The application specifically discloses formulations comprising formoterol fumarate dispersed in HFA 134a, HFA 227 or mixtures thereof and 1 to 3% ethanol. It is stated that it is important to ensure the formoterol fumarate does not come into contact with high concentrations e.g. above 10% w/w, of ethanol since the drug would dissolve leading to instability and crystal growth problems in the final formulation and that the maximum concentration of ethanol during formulation is preferably less than 5%. It is stated that aerosol compositions consisting of formoterol fumarate, HFA 134a and ethanol have proved to be extremely sensitive to ethanol concentration and an ethanol concentration of 3.5% w/w may cause unacceptable crystal growth.

WO 98/52542 discloses a pharmaceutical compositions comprising a therapeutically effective amount of a compound of the formula (I):

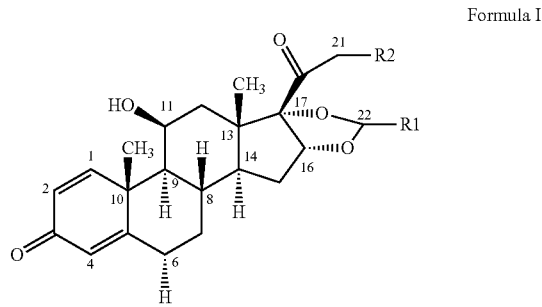

Formula I wherein R1 is 2-propyl, 1-butyl, 2-butyl, cyclohexyl or phenyl; and R2 is acetyl or isobutanoyl and a hydrofluorocarbon propellant, preferably selected from 1,1,1,2-tetrafluoroethane, 1,1,1,2,3,3,3-heptafluoropropane and a mixture thereof, and cosolvent, preferably ethanol, in an amount effective to solubilize the compound of formula (I) and optionally a surfactant. The application specifically discloses solution formulations comprising ciclesonide (1 to 5 mg/ml)

in HFA 134a, HFA 227 or mixtures of HFA 134a and HFA 227 and 5 to 20% by weight ethanol.

Despite the various approaches used in formulating drugs for use in aerosol inhalation, a number of serious difficulties and uncertainties are still often encountered in attempting to develop a physically and chemically stable HFA 134a and/or HFA 227 based formulation that reliably delivers an accurate dose of drug having the proper particle size range. In particular formoterol is reported to be very sensitive in HFA 134a and/or HFA 227 propellant. Up to date no medicinal aerosol formoterol product based on HFA technology is available on the market.

SUMMARY OF THE INVENTION

There is a need for a HFA 134a and/or HFA 227 based medicinal aerosol product containing formoterol and ciclesonide that is chemically and physically stable and that is suitable for delivery to the respiratory system of a patient.

Surprisingly it has been found that it is possible to provide physically and chemically stable formulations suitable for aerosol administration comprising therapeutically effective amounts of formoterol and ciclesonide in suspension in HFA 134a and/or HFA 227 propellant.

Accordingly in one aspect of the present invention there is provided a pharmaceutical suspension formulation suitable for aerosol administration comprising particles of micronized formoterol or a pharmaceutically acceptable salt, solvate or physiologically functional derivative thereof, said particles being suspended in the formulation and particles of micronized ciclesonide or a pharmaceutically acceptable salt, solvate or physiologically functional derivative thereof, said particles being suspended in the formulation and a propellant selected from 1,1,1,2-tetrafluoroethane, 1,1,1,2,3,3,3-heptafluoropropane and a mixture thereof.

Preferred formulations according to the invention exhibit substantially no growth in particle size or change in crystal morphology of the formoterol and/or ciclesonide over a prolonged period, are readily redispersible, and upon redispersion do not flocculate so quickly as to prevent reproducing dosing of ciclesonide and/or formoterol.

In addition to stability the formulations according to the invention provide a significant unexpected therapeutic benefit, particularly a synergistic therapeutic benefit, in the treatment of inflammatory or obstructive airways diseases. In particular, it has been found that compositions containing ciclesonide and formoterol induce an anti-inflammatory activity which is significantly greater than that induced by ciclesonide and formoterol alone and that the amount of ciclesonide needed for a given anti-inflammatory effect may be significantly reduced when used in admixture with formoterol, thereby reducing the risk of undesirable side effects from the repeated exposure to the steroid involved in the treatment of inflammatory of obstructive airways diseases. Furthermore, using the compositions of the invention, pharmaceutical compositions, which have a rapid onset and a long duration of action may be prepared. In particular the combination therapy according to the inventions permits the establishment of a twice daily, in particular once daily dosing regimen with consequent substantial benefits in, for example the treatment of obstructive or inflammatory airways diseases (e.g. higher patent compliance, less side effects).

Ciclesonide (hereinafter also referred to as active ingredient) is the INN for a compound with the chemical name [11β,16α(R)]-16,17-[(Cyclohexylmethylen)bis(oxy)]-11-hydroxy-21-(2-methyl-1-oxopropoxy)pregna-1,4-dien-3, 20-dion. Ciclesonide and its preparation are disclosed in DE 4129535. Ciclesonide as used herein also includes, pharmaceutically acceptable salts of ciclesonide, solvates of ciclesonide, physiologically functional derivatives of ciclesonide or solvates thereof. By the term "physiologically functional derivative" is meant a chemical derivative of ciclesonide having the same physiological function as ciclesonide, for example, by being convertible in the body thereto or by being an active metabolite of ciclesonide. Physiological functional derivatives of ciclesonide which may be mentioned in connection with the invention are for example the 21-hydroxy derivative of ciclesonide with the chemical name 16α,17-(22R,S)-Cyclohexylmethylendioxy-11β,21-dihydroxypregna-1,4-dien-3,20-dion, in particular 16α,17-(22R)-Cyclohexylmethylendioxy-11β,21-dihydroxypregna-1,4-dien-3,20-dion. This compound and its preparation are disclosed in WO 94/22899.

Formoterol (hereinafter also referred to as active ingredient) is the compound N-[2-hydroxy-5-(1-hydroxy-2-((2-(4-methoxyphenyl)-1-methylethyl) amino)ethyl) phenyl] formamide, and is disclosed in U.S. Pat. No. 3,994,974. Formoterol as used herein also includes, pharmaceutically acceptable salts of formoterol, solvates of formoterol, physiologically functional derivatives of formoterol or solvates thereof. As would be appreciated by the skilled person, formoterol may exist in form of different stereoisomers. The present invention includes all stereoisomers of formoterol either in substantially pure form or admixed in any proportions. In one embodiment of the invention, formoterol is present in the formulations according to the invention essentially as R,R-formoterol. Essentially as R,R-formoterol in connection with the present inventions refers to a ratio of R,R-formoterol in a mixture of stereoisomers of formoterol of at least 95%, preferably at least 99%. Stereoisomers of formoterol are for example disclosed in WO98/21175, WO 99/17754, U.S. Pat. No. 6,068,833 and U.S. Pat. No. 5,795, 564. By the term "physiologically functional derivative" is meant a chemical derivative of formoterol having the same physiological function as the free compound, for example, by being convertible in the body thereto. Suitable salts according to the invention include those formed with both organic and inorganic acids. Pharmaceutically acceptable acid addition salts include but are not limited to those formed from hydrochloric, hydrobromic, sulphuric, citric, tartaric, phosphoric, lactic, pyruvic, acetic, trifluoroacetic succinic, oxalic, fumaric, maleic, oxaloacetic, methanesulphonlc, ethanesulphonic, p-toluenesulphonic, benzenesulphonic, isethionic, and naphthalenecarboxylic, such as 1-hydroxy-2-naphthalenecarboxylic acids. Formoterol fumarate and R,R-formoterol fumarate are preferably mentioned in connection with the invention.

As mentioned above, both ciclesonide and formoterol and their pharmaceutically acceptable salts, solvates, and physiologically functional derivatives have been described for use in the treatment of respiratory diseases. Therefore, formulations of ciclesonide and formoterol and their pharmaceutically acceptable salts, solvates, and physiologically functional derivatives have use in the prophylaxis and treatment of clinical conditions for which a selective %-adrenoreceptor agonist and/or a glucocorticosteroid is indicated. Such conditions include diseases associated with reversible airways obstruction such as asthma, nocturnal asthma, exercise-induced asthma, chronic obstructive pulmonary diseases (COPD) (e.g. chronic and wheezy bronchitis, emphysema), respiratory tract infection and upper respiratory tract disease (e.g. rhinitis, such as allergic and seasonal rhinitis).

Accordingly, the present invention provides a method for the prophylaxis or treatment of a clinical condition in a mammal, such as a human, for which a selective $\beta_2$-adrenoreceptor agonist and/or glucocorticosteroid is indicated, which comprises administration of a therapeutically effective amount of a pharmaceutical formulation according to the invention comprising formoterol or a pharmaceutical acceptable salt, solvate, or physiologically functional derivative thereof and ciclesonide or a pharmaceutical acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease.

The amount of formoterol and ciclesonide, or a pharmaceutical acceptable salt, solvate or physiologically functional derivative thereof which is required to achieve a therapeutic effect will, of course, vary with the particular compound, the subject under treatment, and the particular disorder or disease being treated. As a monotherapy, formoterol fumarate is generally administered to adult humans by aerosol inhalation at a dose of 6 μg to 12 μg (corresponding to 4.9 μg to 9.8 μg formoterol) twice daily or up to 24 μg twice daily. As a monotherapy, ciclesonide is generally administered to adult humans by inhalation at a daily dose of from 0.05 mg to 1.6 mg, which can be administered in one or several doses.

It is preferred in connection with the present invention to have a twice daily dosing regimen. Surprisingly it has been found that formoterol in combination with ciclesonide may be effectively administered as a once daily dosing regimen. Further subject of the invention therefore is also combination of ciclesonide with formoterol in the form of once daily dosing regimen.

Suitably, the pharmaceutical formulations which are suitable for inhalation according to the invention comprise the active ingredients in amounts such that in case of administration by inhalation from inhalers each actuation provides a therapeutically effective dose, for example, a dose of formoterol fumarate of 4 μg to 24 μg, preferably 6 μg to 12 μg and a dose of ciclesonide of 10 μg to 1600 μg, preferably 40 μg to 800 μg, more preferably, 50 μg to 400 μg. It is particularly preferred that each actuation provide a dose therapeutically effective for a twice daily dosing regiment or more particularly preferred for a once daily dosing regimen.

Pharmaceutical formulations according to the invention, depending on the valve chamber to be used, may suitably contain from about 0.2 mg to about 8 mg ciclesonide per ml, preferably from 1 mg to 4 mg per ml. Ciclesonide may be formulated in different strength of doses e.g. 1 mg per ml, 2 mg per ml or 4 mg per ml. Formoterol may be present in the formulations according to the inventions from about 0.04 mg to 0.5 mg formoterol per ml, preferably from 0.09 mg to 0.4 mg formoterol per ml and may be formulated in different strength doses as well.

The pharmaceutical formulations according to the invention may further include other therapeutic agents for example anticholinergics such as ipatropium and tiotropium, pharmaceutically acceptable salts salts or solvents thereof. Examples, which may be mentioned are ipatroplum bromide and tiotropium bromide and solvates thereof.

Suitably, the pharmaceutical formulations which are suitable for inhalation according to the invention provide therapeutically effective doses that permit the establishment of a twice daily (bis in diem—b. i. d) dosing regimen and in particular a once daily dosing regimen.

Suspension aerosol formulation refers to a formulation in which the drug is in particulate form and is substantially insoluble in the formulation.

Propellant systems for aerosol formulations based on HFA 134a (1, 1, 1, 2-terafluorethane) and HFA 227 (1, 1, 1, 2, 3, 3, 3-heptafluoropropane) are disclosed in, for example, EP 0372777, WO91/04011, WO91/11173, WO91/11495, WO91/14422, WO93/11743, and EP-0553298. These applications are all concerned with the preparation of pressurised aerosols for the administration of medicaments and seek to overcome problems associated with the use of this new class of propellants, in particular the problems of stability associated with the pharmaceutical formulations prepared. The applications propose, for example, the addition of one or more of excipients such as polar cosolvents or wetting agents (e.g. alcohols such as ethanol), alkanes, dimethyl ether, surfactants (including fluorinated and non-fluorinated surfactants, carboxylic acids such as oleic acid, polyethoxylates etc.) or bulking agents such as a sugar (see for example WO02/30394) and vehicles such as salts of cromoglicic acid and/or nedocromil which are contained at concentrations, which are not therapeutically and prophylactically active (see WO00/07567).

The formulations according to the invention may contain additional excipients as mentioned above.

In a preferred embodiment of the invention the formulations contain a wetting agent, preferably ethanol and optionally a surfactant, preferably oleic acid. The presence of the ethanol assist in the stability, the general performance and in the manufacturing of the formulation. Ethanol is preferably present in concentration range, which does not lead to dissolution of the ciclesonide in the propellant formulation and does not cause undesired effects on formoterol. Preferably ethanol is present in the formulations according to the invention below 3% (w/w), more preferably below 2%, particularly preferable below 1%, and most preferably below 0.5%.

The aerosol formulations according to the invention may preferably contain surfactant. Suitable surfactants are known in the art and include oleic acid, sorbitantrioleate and lecithin. A preferred surfactant is oleic acid. The amount of surfactant, which may be present in the formulation according to the invention is usually in the range of about 0.001% to 0.1% (w/w).

In another embodiment the formulations according to the invention additionally contain a bulking agent and/or vehicle. Examples of bulking agents which may be mentioned in connection with the invention are sugar (such as lactose, lactose monohydrate, glucose, D+ trehalose dehydrate), DL-alanine and/or ascorbic acid. Suitable bulking agents are also disclosed in WO02/30394. The weight ratio of active ingredient (ciclesonide and formoterol) to bulking agent is generally in the range of 1:0.1 to 1:100, preferably 1.3 to 1:40. The bulking agent is preferably present in micronized form with a mean particle size diameter of less than 100 microns, desirably less than 20 microns, and preferably in the range 1 to 10 microns, for example, 1 to 5 microns. In a preferred embodiment the mean particle size diameter is below 1 micron such as described in WO02/30394.

In another embodiment of the invention the formulations according to the inventions additionally contain vehicles such as pharmaceutically acceptable salts of cromoglicic acid and/or nedocromil which are contained at concentrations, which are not therapeutically and prophylactically active (see WO00/07567). In a preferred embodiment the salt of cromoglicic acid is the disodium salt (disodium chromoglycate) and the salt of nedocromil is the sodium salt. These vehicles are generally present in the range of 10:1 to 1:10 by weight based on the weight of the active ingredients. These vehicles are also present preferably in micronized form with a mean particle size diameter of preferably less than 10 microns. However they may also be present with greater particle sizes.

The active ingredients (ciclesonide and formoterol respectively) present as particles in the formulations according to the invention should be in a form so as to permit inhalation of substantially all of the active ingredients into the lungs upon administration of the aerosol formulation. Thus the active ingredients should—unless obtainable by chemical processes in a suitable size—be micronized so as to permit inhalation of substantially all of the active ingredients into the lungs upon administration of the aerosol formulation. Thus the active ingredients will have a mean particle size diameter of less than 100 microns, desirably less than 20 microns, and preferably in the range 1 to 10 microns, for example, 1 to 5 microns.

The formulations according to the invention may be prepared by adding the required quantity of active ingredients into an aerosol vial, crimping a valve on the vial and introducing propellant or optionally a pre-mixed blend of propellant and optionally further excipients such as surfactant through the valve. Alternatively the active ingredients may be added to a chilled propellant or optionally a pre-mixed blend of propellant and optionally further excipients and dispersed using a suitable mixer. After homogenisation the suspension can be filled into aerosol vials and the vial closed by crimping a valve on the vial.

Canisters generally comprise a container capable of withstanding the vapour pressure of the propellant, such as plastic or plastic-coated glass bottle or preferably a metal can, for example an aluminium can which may optionally be anodised, lacquer-coated and/or plastic-coated, which container is closed with a metering valve. It may be preferred that canisters be coated with a fluorocarbon polymer as described in WO 96/32150, for example, a co-polymer of polyethersulphone (PES) and polytetrafluoroethylene (PTFE). Another polymer for coating that may be contemplated is FEP (fluorinated ethylene propylene).

The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Thermoplastic elastomer valves as described in WO92/11190 and valves containing EPDM rubber as described in WO95/02650 are especially suitable. Suitable valves are commercially available from manufacturers well known in the aerosol industry, for example, from Valois, France (eg. DF10, DF30, DF60), Bespak pic, UK (eg. BK300, BK356, BK357) and 3M-Neotechnic Ltd, UK (eg. Spraymiser).

Valve seals, especially the gasket seal and also the seals around the metering chamber, will preferably be manufactured of a material, which is inert to and resists extraction into the contents of the formulation, especially when the contents include ethanol.

Valve materials, especially the material of manufacture of the metering chamber, will preferably be manufactured of a material which is inert to and resists distortion by contents of the formulation, especially when the contents include ethanol. Particularly suitable materials for use in manufacture of the metering chamber include polyesters eg polybutyleneterephthalate (PBT) and acetals, especially PBT.

Materials of manufacture of the metering chamber and/or the valve stem may desirably be fluorinated, partially fluorinated or impregnated with fluorine containing substances in order to resist drug deposition.

Valves, which are entirely or substantially composed of metal components (eg Spraymiser, 3M-Neo-technic), are especially preferred for use according to the invention.

It should be understood that in addition to the ingredients particularly mentioned above, the formulations of this invention may include other agents conventional in the art having regard to the type of formulation in question. Furthermore, the claimed formulations include bioequivalents as defined by the US Food and Drugs Agency.

Amounts expressed in percent (%) refer to percent of weight, based on the total weight of the formulation (w/w) unless stated differently.

The invention will now be illustrated by the following examples without restricting it.

EXAMPLE 1

Metered Dose Inhaler

A solution of 1.07 g ethanol and of 250 g TG 227 is liquified by cooling to a temperature of approx. −50° C. in a stainless steel vessel. 1.428 g micronized Ciclesonide is transferred into the vessel and dispersed in the ethanol/propellant mixture using a high shear mixer. 200 g TG 227 is filled into a batching vessel and liquified by cooling to a temperature of approx. −50° C. 0.214 g micronized disodium cromoglycate is transferred into the batching vessel and dispersed using a high shear mixer. 0.043 g formoterol fumarate dihydrate is added to the chilled suspension. The suspension is further dispersed using the high shear mixer. The ciclesonide suspension in ethanol/TG227 is then transferred into the batching vessel. The suspension is homogenized for sufficient time to give a homogenous suspension. TG 227 is added to the suspension to a total weight of 500 g. While cooling and stirring the suspension is filled in aluminum cans and a 50 µl metering valve is crimped into place. Each actuation of 70 mg delievers 200 µg of ciclesonide and 6 µg of formoterol fumarate.

EXAMPLE 2

Metered Dose Inhaler

A solution of 1.07 g ethanol and of 250 g TG 227 is liquified by cooling to a temperature of approx. −50° C. in a stainless steel vessel. 1.428 g micronized Ciclesonide is transferred into the vessel and dispersed in the ethanol/propellant mixture using a high shear mixer. 200 g TG 227 is filled into a batching vessel and liquified by cooling to a temperature of approx. −50° C. 0.043 g formoterol fumarate dihydrate is transferred into the batching vessel and dispersed using a high shear mixer. The ciclesonide suspension in ethanol/TG227 is then transferred into the batching vessel. The suspension is homogenized for sufficient time to give a homogenous suspension. TG 227 is added to the suspension to a total weight of 500 g. While cooling and stirring the suspension is filled in aluminum cans and a 50 µl metering valve is crimped into place. Each actuation of 70 mg delievers 200 µg of ciclesonide and 6 µg of formoterol fumarate.

EXAMPLE 3

Metered Dose Inhaler 0.05 g of oleic acid is dissolved in 1.07 g ethanol. 250 g of TG 227 are added and the mixture is liquified by cooling to a temperature of approx. −50° C. in a stainless steel vessel.

1.428 g micronized Ciclesonide is transferred into the vessel and dispersed in the ethanol/propellant mixture using a high shear mixer. 200 g TG 227 is filled into a batching vessel and liquified by cooling to a temperature of approx. −50° C. 0.043 g formoterol fumarate dihydrate is transferred into the batching vessel and dispersed using a high shear mixer. The ciclesonide suspension in ethanol/TG227 is then transferred into the batching vessel. The suspension is homogenized for sufficient time to give a homogenous suspension. TG 227 is added to the suspension to a total weight of 500 g. While cooling and stirring the suspension is filled in aluminum cans and a 50 µl metering valve is crimped into place. Each actuation of 70 mg delievers 200 µg of ciclesonide and 6 µg of formoterol fumarate.

Although the invention has been described in terms of preferred formulations and ingredients, it will be understood that these are not intended to be limiting. To the contrary, those skilled in the art will understand that various optional ingredients may be included, such as flavouring agents, preservatives, additional active ingredients, and the like, while still embodying the present invention.

The invention claimed is:
1. A pharmaceutical suspension formulation comprising:
a) as a first active ingredient, particles of R,R-formoterol or a pharmaceutically acceptable salt thereof, said particles being suspended in the formulation,
b) as a second active ingredient, particles of ciclesonide or a pharmaceutically acceptable salt thereof, said particles being suspended in the formulation,
c) a propellant selected from the group consisting of 1,1,1,2-tetrafluoroethane, 1,1,1,2,3,3,3-heptafluoropropane and a mixture thereof, and
d) disodium cromoglycate at a concentration which is not therapeutically and/or prophylactically active,
wherein said first active ingredient and said second active ingredient are the sole active ingredients in said pharmaceutical suspension formulation, and are readily dispersible, and upon redispersion do not flocculate as to prevent reproducing dosing of said first active ingredient and/or said second active ingredient.

* * * * *